United States Patent [19]

Reed et al.

[11] 4,153,516

[45] May 8, 1979

[54] PROCESS FOR SEPARATING ALKOXYKETONE COMPOUNDS FROM THE CORRESPONDING 1-ALKOXY-2-ALKANOL COMPOUND

[75] Inventors: Denvil E. Reed; Richard C. Grimm, both of Charleston, W. Va.

[73] Assignee: Union Carbide Corporation, New York, N.Y.

[21] Appl. No.: 822,197

[22] Filed: Aug. 5, 1977

[51] Int. Cl.² .......................... B01D 3/40; C07C 49/24
[52] U.S. Cl. ........................................ 203/64; 203/81; 203/84; 203/63; 260/594
[58] Field of Search ...................... 203/63, 64, 81, 82, 203/84; 260/594, 643 R

[56] References Cited

U.S. PATENT DOCUMENTS

| 2,805,983 | 9/1957 | Horsley | 203/63 |
| 3,625,836 | 12/1971 | Stansbury et al. | 260/594 |

FOREIGN PATENT DOCUMENTS 2526748 12/1976 Fed. Rep. of Germany ........... 260/594

Primary Examiner—Wilbur L. Bascomb, Jr.
Attorney, Agent, or Firm—Robert C. Brown

[57] ABSTRACT

A process for recovering alkoxyketone compounds from mixtures of the alkoxyketone compound and the corresponding 1-alkoxy-2-alkanol compound by extractive distillation with diols, triols and polyols as extractants.

13 Claims, 1 Drawing Figure

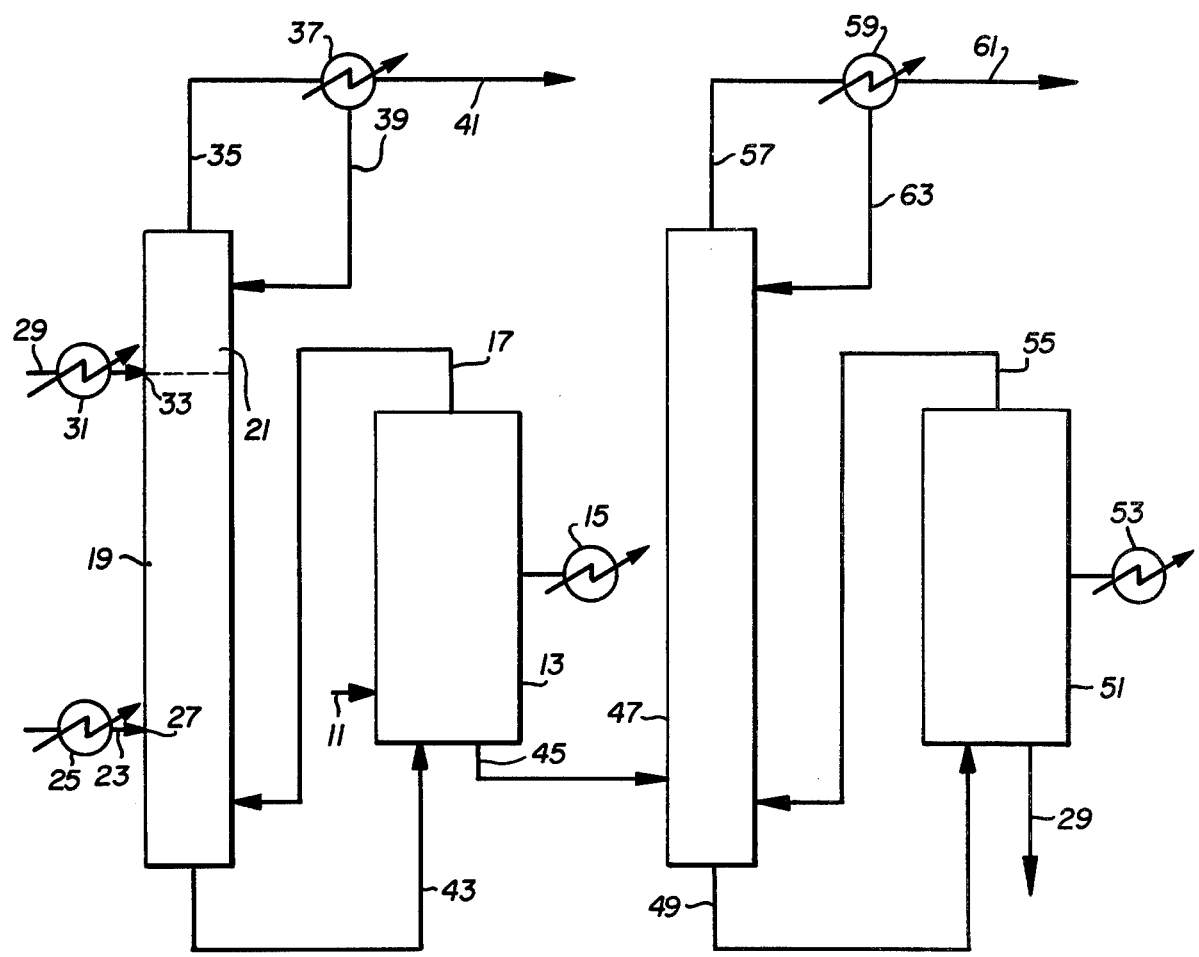

PROCESS FOR SEPARATING ALKOXYKETONE COMPOUNDS FROM THE CORRESPONDING 1-ALKOXY-2-ALKANOL COMPOUND

BACKGROUND OF THE INVENTION

This invention relates to a method recovering alkoxyketone compounds having a high degree of purity from a mixture of an alkoxyketone compound and the corresponding 1-alkoxy-2-alkanol compound.

The most common form of preparing alkoxyketone compounds is to catalytically dehydrogenate the corresponding 1-alkoxy-2-alkanol compound in the vapor phase. When such a preparative method is used, problems of separation arise. The difficulties surrounding the separation of an alkoxyketone compound from admixture with the corresponding 1-alkoxy-2-alkanol have been primarily due to the formation of a binary azeotrope composition.

This difficulty has been noted in the past and a variety of solutions have been proposed in an attempt to obtain alkoxyketone compounds of high purity. Heretofore, the separation has been effectuated either by chemical modification followed by distillation or by multistep azeotropic distillative methods. For example, U.S. Pat. No. 2,170,855 discloses a chemical modification method in which an organic acid or anhydride is added to a reaction mixture of an alkoxyacetone compound and the corresponding 1-alkoxy-2-propanol compound resulting in the formation of the high boiling ester derivative of the 1-alkoxy-2-propanol starting material. The resulting mixture is distilled and redistilled to recover the desired alkoxyacetone.

Alternatively, U.S. Pat. Nos. 2,795,873 and 3,525,735, respectively, discloses azeotropic distillation processes in which either an unsubstituted monohydric alcohol or water is added to the reaction mixture in order to break the minimum boiling point binary azeotrope. In these processes, a new lower boiling binary azeotrope is formed between the azeotropic solvents and the alkoxyacetone compound which may then be removed from the binary azeotropic mixture by distillation.

Although, they seem relatively simple and efficient, the prior art processes suffer from one or more inherent limitations and disadvantages. For example, it is generally recognized that both of the previously disclosed processes usually give rise to alkoxyketone compounds that are contaminated with unacceptable amounts of the corresponding 1-alkoxy-2-alkanol compound. In addition, the azeotropic distillation process requires large expenditures of energy due to the very high latent heat of the azeotropic solvents, as well as, time consuming and cumbersome purification procedures to remove the desired alkoxyketone compound from the azeotropic solvent. Consequently there exists a need for a fast and more efficient single step process for separating alkoxyketone compounds from the corresponding 1-alkoxy-2-alkanol compound with enhanced purity of the alkoxyketone compound coupled with low energy requirements.

SUMMARY OF THE INVENTION

According to the present invention there is provided a process for separating an alkoxyketone compound from a feed mixture of the alkoxyketone compound and the corresponding 1-alkoxy-2-alkanol compound which comprises:

A. introducing an extractant solvent selected from the group of aliphatic diol, triol and polyol compounds having from 2 to 6 carbon atoms and monohydric aliphatic alcohols having from 5 to 10 carbon atoms into an extractive distillation zone;

B. introducing the feed mixture into the extractive distillation zone at a point above the bottom thereof and below the extractant solvent point of entry;

C. subjecting the resulting mixture to extractive distillation in the extractive distillation zone; and D. recovering at the top of the extractive distillation zone a distillate fraction comprised of the alkoxyketone and the extractant solvent, substantially free of the corresponding 1-alkoxy-2-alkanol compound.

The process of this invention provides excellent separation under mild process conditions, using very little equipment and has the advantage of very short separation times and minimum energy expenditures.

BRIEF DESCRIPTION OF THE DRAWING

The FIGURE is a schematic flow diagram of an illustrative embodiment of the present invention.

DESCRIPTION OF THE PREFERRED EMBODIMENTS

The alkoxyketone compounds contemplated for use in the process of this invention are lower alkoxyketone compounds having from 4 to 10 carbon atoms. Illustrative of alkoxyketone compounds which can be separated from the corresponding 1-alkoxy-2-alkanol compound are methoxyacetone, ethoxyacetone, n-proproxyacetone, isopropoxyacetone, n-butoxyacetone, tert-butoxyacetone, methoxy-2-butanone, ethoxy-2-butanone and the like.

Compounds which are useful as extractant solvents in the conduct of the process of this invention are diol or triol or polyol compounds which contain from 2 to about 6 carbon atoms. Preferred extractant solvents are diol or triol compounds having from 2 to about 6 carbon atoms, with those diol compounds having 2 or 3 carbon atoms and glycerine being particularly preferred. Illustrative of useful extractant solvents are linear diol compounds such as ethylene glycol; 1,2-propylene glycol; 1,3-propylene glycol, 1,2-dihydroxypentane; 1,3-butanediol, 1,4-butanediol, 2,3-dihydroxypentane, 1,3-dihydroxypentane; 2,4-pentanediol, 1,5-pentanediol, 1,2-dihydroxy-3-methylpentane, 1,6-hexanediol, 1,2-hexanediol, 2,5-hexanediol and the like. Illustrative of useful cyclic diols are 1,2-cyclopentanediol; 1,2-dihydroxy-4-ethyl-5-propylcyclohexane and the like. Useful triol extractant solvents include glycerine, 2,4,6-trihydroxyhexane, 1,2,6-hexanetriol or the like.

Still other suitable extractant solvents are monohydric primary aliphatic alcohols having from 5 to about 8 carbon atoms; monohydric aliphatic secondary alcohols having from 5 to about 8 carbon atoms and alicyclic alcohols having 5 or 6 carbon atoms in the ring with a total of from 6 to about 8 carbon atoms. Illustrative of useful monhydric extractant solvents are pentanols, hexanols, heptanols, octanols, secondary pentanols, secondary hexanols, cyclopentanols and cyclohexanols.

The ratio of feed mixture to the extractant solvent which is employed to effectuate the desired separation is not narrowly critical. It will be appreciated that this ratio may vary depending upon the particular extractant solvent employed, the composition of the feed mixture, the degree of separation desired and other operating parameters, such as temperature and pressure. In general, the extractant solving to feed ratio may vary from about 1 to 1 to about 100 to 1, by volume depending on the foregoing factors. It should be appreciated that while no practical advantages are derived from the use of ratios outside of the stated range, these ratios are still within the contemplation of this invention, although they are not generally advantageous.

The preferred extractant solvent employed in a particular situation is conventionally determined from a consideration of the relative volatility of the components in the feed mixture at any specific concentration; the relative volatility of the components in the feed mixture in the extractant solvent and the boiling point of the extractant solvent. The relative volatility of the components being separated in the feed mixture in the extractant is at least 0.6 units higher than the volatility of the feed mixture at a specific concentration; and the boiling point of the exrtractant solvent is at least 20° C. higher than the boiling point of the highest boiling component of the feed mixture.

In order to obtain alkoxyacetone compounds of approximately 99 percent purity from feedstock containing 60-65% alkoxyacetone, the process of this invention is to be carried out with a solvent-to-reflux ratio of not less than 1.5 and a reflux-to-make ratio of not less than 1.0. The preferred ratios may be obtained by a simple manipulation of temperatures, pressures, and other process parameters.

To inhibit the formation of 2-alkyl alkoxyalkyl-1, 3-dioxolane contaminants, an organic or inorganic base is preferably added to the feed mixture in an amount sufficient to raise the pH to 8 or greater. The base serves to neutralize the slight acidity of the extractive solvent thereby lowering the production of the dioxalane contaminant from as high as five percent to less than 0.5 percent.

Distallation pressures are not critical. The process can be conducted at either subatmospheric, atmospheric or superatmospheric pressure. For convenience the process is usually conducted at atmospheric pressure. This obviates the necessity of employing vacuum equipment and expensive refrigeration equipment which may be necessary to operate at exceedingly reduced pressures.

The temperature at which the process of this invention is conducted is not narrowly critical. Process temperatures may vary widely depending on process pressure; extractant solvent; composition of the feed mixture and the ratio of extractant solvent to feed mixture. In general, the maximum process temperature is equal to the boiling point of the extractive solvent of the specific pressure of operation. The minimum process temperature is equal to the boiling point of the feed component having the lower boiling point at the specific pressure of operation. As is well known a constant process temperature is not maintained throughout the extractive distillation zone. A high temperature which approximates that of the extractant solvent is present at the bottom of the extractive distillation zone, a low temperature which approximates the boiling point of the lower boiling component of the feed mixture is present at the top of the extractive distillation zone and an intermediate temperature is present in the middle of the zone.

The process of this invention can be conducted in a batch, semi-continuous or continuous fashion using counter-current contacting devices.

The feed mixture and extractant solvent can be introduced into the extraction zone continuously or intermittently introduced into the extractive distillation zone during the course of the process. The process of this invention is preferably conducted in a continuous distillation.

In the preferred embodiments of this invention, the extractant solvent is introduced at a point below the top of the multistage distillation column. The portion of the column below the extractant solvent point of entry functions as the extractive distillation zone and the portion of the column above the extractant solvent point of entry functions to remove the contaminating solvent from the alkoxyketone component.

Means to introduce and/or adjust the quantity of feed and/or solvent introduced, either intermittently or continuously into the extraction zone during the course of the process can be conveniently utilized to maintain the desired volume ratios of the feed mixture and extractant solvent. The process can be carried out in a single extraction zone or a plurality of extractive distillation zones. The materials of construction employed should be inert to the components of the feed mixture and to the extractant solvent and the frabrication of the equipment should be able to withstand process temperatures and pressures.

The apparatus employed in the process for the main extraction and for the optional solvent recovery distillation is conventional e.g., an extraction column of the multistage type containing a plurality of perforated plates, or a packed column, a bubble cap tray column or any conventional type distillation column used in multistage distillation or counter-current contacting.

In the process of this invention the extractant solvent is introduced at or near the top of the extractive distillation column and the feed mixture is introduced at or near the middle of the column. The feed mixture is then subjected to extractive distillation within the column which results in the separation of the two components of the feed mixture. The alkoxyketone component contaminated with minor amounts of the extractant solvent is collected overhead. The extractant solvent can be removed from the alkoxyketone compound in a subsequent batch, semi-continuous or continuous mode distillation if it is not adequately removed by a solvent- removal section or zone above the extractive zone of the extractive distillation column.

The preferred embodiments of the process of this invention is illustrated by the schematic flow sheet outlining in the figure for separating alkoxyacetone from 1-alkoxy-2-propanol in a continuous fashion. Referring to the drawing:

Feedstock, extractant solvent or a mixture thereof is initially charged into kettle 13 via line 11, where it is heated to its boiling point by heat exchanger 15. Vapors percolate from kettle 13 and are introduced via line 17, into multistage extractive distillation zone 19. Vapor is then allowed to percolate up extractive distillation zone 19 to a point above the extractant solvent point of entry 33, at which time the system is allowed to equilibrate for from about ¼ to about 2 hours.

The system is now capable of being operated in a continuous manner. Feedstock comprised of alkoxyacetone and the corresponding 1-alkoxy-2-propanol compound is continuously introduced via line 23 into heat exchanger 25, where it is preheated to a temperature to within ± 10° C. of the steady-state temperature of multistage extractive distillation zone 19 at feedstock point of entry 27. The preheated feedstock continues through line 23 entering multistage extractive distillation zone 19, at feedstock point of entry 27. The feedstock flows into multistage extractive distillation zone 19, contacting upward percolating vapors entering multistage extractive distillation zone 19 via line 17. The vapors and the feedstock exchange heat producing a vapor fraction rich in the alkoxyacetone component with lessor amounts of the 1alkoxy-2-propanol component and extractive solvent. The combined vapors, i.e. extractant solvent, alkoxyacetone and 1-alkoxy-2-propanol percolate up multistage extractive distillation zone 19. A fraction of the combined vapors condenses at each stage of the multistage extractive distillation zone 19, producing a liquid vapor steady state equilibrium at each stage. The amount or concentration of 1-alkoxy-2-propanol in vapor phase becomes progressively less at each successive stage. Simultaneously with the introduction of the feedstock, extractant solvent is introduced via line 29 into heat exchanger 31 where it is preheated to within 10° C. of the temperature of extraction zone 19 at extractant solvent point of entry 33. Extractant solvent percolates down multistage extractive distillation zone 19, coming into counter-current contact with the upward percolating vapors. The extractant solvent dissolves and removes the alkoxy-2-propanol component with a small fraction of the alkoxyacetone component as the solvent percolates down multistage extractive distillation zone 19. The remaining vapors, alkoxyacetone and extractant solvent, continue to the upper portion of multistage extractive distillation zone 19, where the vapors are fractionated into a vapor phase which is substantially alkoxyacetone with minor amounts of extractant solvent. The vapors percolate above solvent point of entry into solvent-removal distillation zone 21, where the vapors are fractionated into a vapor phase which is alkoxyacetone having a purity of about 99 percent by weight.

The vapor phase leaves the top of solvent removal distillation zone 21 via line 35 into heat exchanger 37 where it is condensed. A fraction of the condensed alkoxyacetone continues through line 39 into solvent removal distillation zone 21 as reflux and the remaining fraction continues through line 41 to be collected as substantially pure alkoxyacetone.

As noted above, the extractant solvent percolates down multistage extractive distillation zone 19 carrying with it the major portion of 1-alkoxy-2-propanol component and a fraction of the alkoxyacetone component.

In the lower portion of the extraction zone 19, the solvent solution comes in countercurrent contact with vapors of the components and extractant solvent that enter multistage extractive distillation zone 19 through line 17. The vapors percolate up extraction zones progressively vaporizing and purifying the downflowing solution of the remaining alkoxyacetone fraction which combines with the combined vapors described above.

The remaining solution, i.e., the liquid downflow, comprised of extractant solvent and 1-alkoxy-2-propanol with very minor amounts of alkoxyacetone percolates down multistage extractive distillation zone 19.

The liquid leaves the bottom of multistage extractive distillation zone 19 via line 43 and enters kettle 13 where a fraction of the liquid is vaporized and is taken overhead via line 17 into multistage extractive distillation zone 19 to repeat in a continuous fashion the extractive distillation cycle described hereinabove. The balance of the liquid entering kettle 13 leaves the bottom via line 45 into solvent recovery column 47.

Extractant Solvent is initially charged into kettle 51, where it is heated to its boiling point by heat exchanger 53. Extractant solvent vapors pass over head via line 55 into solvent recovery column 47, where they are allowed to equilibrate.

As pointed out above, the liquid enters solvent recovery column 47, where it flows downward and comes into countercurrent contact with upward, percolating, extractant solvent vapors entering solvent recovery column 47 via line 55. A portion of the liquid, rich in the 1-alkoxy-2-propanol component, is vaporized on each stage or tray of the column and eventually passes overhead via line 57 through heat exchanger 59 where it is condensed and cooled to approximately room temperature. One portion of the condensed distillate is collected from line 61 and the other portion returns to solvent recovery column 47 via line 63 to maintain reflux conditions. The down-flowing liquid, rich in extractant solvent combines with condensed extractant solvent vapor and proceeds along line 49 into kettle 51. A portion flashes on entering kettle 51 and passes over head via line 55 to continue the above described solvent purification cycle in a continuous fashion. The remainder passes as a liquid via line 29, where it is recycled along line 29 to continue the above described extraction cycle in a continuous fashion.

The manner of practicing the process of the present invention and advantages obtained thereby will be illustrated by the following specific examples which are merely illustrative and are not intended, in any manner, to limit the scope of the invention.

EXAMPLES I–XV

Procedure:

Binary feedstock composed of 65 weight percent methoxyacetone and 32.5 weight percent 1-methoxy-2-propanol was fed into a 43 tray Oldershaw still column at a point 13 trays above the kettle. Ethylene glycol was introduced 38 trays above the kettle. The trays were 28-mm in diameter and encased in silvered vacuum jacket, with 1-inch tray spacings.

The distillate was recovered overhead, and its composition was determined by gas-liquid chromatography on a binary basis.

Process parameters and results are set forth in Table I hereinbelow:

TABLE I

| Ex. | Absolute Pressures, MM Hg. | TEMPERATURE ° C. | | | | | | RATIOS | | | | Analysis, Weight % Methoxyacetone in the (Solvent Distillate (Free basis) |
|---|---|---|---|---|---|---|---|---|---|---|---|---|
| | | Ethylene Glycol | Ethylene Glycol Tray | Feed | Feed Tray | Kettle | Head | Reflux/ Make | Solvent/ Feed | Distillate/ Feed | Solvent/ Reflux | |
| I | 750 | 107 | 105 | 28 | 126 | 196 | 108 | 15.0 | 15.2 | 4.05 | 3.8 | 98.6 |
| II | 750 | 109 | 103 | 28 | 122 | 186 | 107 | 10.0 | 7.5 | — | — | 99.0 |

TABLE I-continued

| Ex. | Absolute Pressures, MM Hg. | TEMPERATURE ° C. | | | | | RATIOS | | | | Analysis, Weight % Methoxy-acetone in the (Solvent Distillate (Free basis) |
| | | Ethylene Glycol | Ethylene Glycol Tray | Feed | Feed Tray | Kettle | Head | Reflux/ Make | Solvent/ Feed | Distillate/ Feed | Solvent/ Reflux | |
| --- | --- | --- | --- | --- | --- | --- | --- | --- | --- | --- | --- | --- |
| III | 750 | 109 | 111 | 28 | 132 | 189 | 114 | 4.0 | 7.5 | — | — | 99.3 |
| IV | 750 | 109 | 104 | 28 | 127 | 181 | 108 | 4.0 | 4.8 | 2.75 | 2.2 | 99.4 |
| V | 750 | 110 | 108 | 28 | 130 | 185 | 112 | 3.0 | 5.0 | 2.76 | 2.4 | 98.3 |
| VI | 750 | 110 | 107 | 28 | 130 | 180 | 113 | 2.5 | 3.7 | 2.31 | 2.2 | 97.3 |
| *VII | 750 | 122 | 121 | 117 | 126 | 185 | 112 | 2.55 | 5.00 | 1.81 | 3.84 | 95.3 |
| *VIII | 750 | 130 | 123 | 119 | 126 | 190 | 114 | 1.01 | 4.38 | 1.39 | 6.25 | 91.6 |
| *IX | 750 | 125 | 132 | 118 | 139 | 190 | 114 | 2.90 | 5.11 | 1.71 | 4.00 | 98.0 |
| *X | 750 | 125 | 132 | 116 | 139 | 188 | 115 | 2.40 | 5.69 | 1.80 | 4.48 | 99.6 |
| *XI | 750 | 124 | 130 | 116 | 138 | 190 | 114 | 2.80 | 5.55 | 2.19 | 3.44 | 98.00 |
| *XII | 750 | 125 | 130 | 115 | 139 | 188 | 114 | 2.00 | 5.43 | 1.71 | 4.76 | 99.6 |
| *XIII | 750 | 125 | 131 | 115 | 141 | 191 | 115 | 1.76 | 5.75 | 1.74 | 5.19 | 96.0 |
| *XIV | 330 | 107 | 103 | 104 | 116 | 163 | 91 | 2.10 | 5.82 | 1.76 | 4.88 | 98.7 |
| *XV | 327 | 102 | 102 | 110 | 112 | 165 | 90 | 2.50 | 7.00 | 2.06 | 4.76 | 99.6 |

*Column had 43 older shaw trays with glycol added at tray 38 and feed at tray 13. All other runs were made with a 40-tray column with glycol added at tray 40 and feed at tray 20.

What is claimed is:

1. A process for separating an alkoxyketone compound from a feed mixture of the alkoxyketone compound and the corresponding 1-alkoxy-2-alkanol compound which comprises:
    (a) introducing an extractant solvent selected from the group of aliphatic diols, triols and polyols having from two to six carbon atoms into an extractive distillation zone;
    (b) introducing said feed mixture into said extractive distillation zone at a point above the bottom thereof and below the point of entry of said extractant solvent;
    (c) subjecting the resulting mixture to extractive distillation in said extractive distillation zone; and
    (d) recovering at the top of said extractive distillation zone a distillate fraction containing alkoxyketone compound and some of said extractant solvent substantially free of the corresponding 1-alkoxy-2-alkanol compound.

2. A process according to claim 1 wherein said feed mixture comprises an alkoxyacetone compound and the corresponding alkoxy-2-propanol compound.

3. A process according to claim 1 wherein said feed mixture comprises methoxy acetone and methoxy-2-propanol.

4. A process according to claim 1 wherein said extractant solvent is ethylene glycol.

5. A process according to claim 1 wherein said extractant solvent is propylene glycol.

6. A process according to claim 1 wherein said extractant solvent is glycerine.

7. A process for separating an alkoxyketone compound from a feed mixture of the alkoxyketone compound and the corresponding 1-alkoxy-2-alkanol compound which comprises:
    A. introducing an extractant solvent selected from the group of aliphatic diols, triols and polyols having from two to six carbon atoms into an extractive distillation zone;
    B. introducing said feed mixture into said extractive distillation zone at a point above the bottom thereof and below the point of entry of said extractant solvent;
    C. subjecting the resulting mixture to extractive distillation in said extractive distillation zone;
    D. recovering at the top of said extractive distillation zone a distillate fraction containing alkoxyketone compound and some of said extractant solvent substantially free of the corresponding 1-alkoxy-2-alkanol compound; and
    E. subjecting said distillate to further distillation to recover said alkoxyketone compound.

8. A process according to claim 7 wherein said feed mixture comprises an alkoxyacetone compound and the corresponding alkoxy-2-propanol compound.

9. A process according to claim 7 wherein said feed mixture comprises methoxy acetone and methoxy-2-propanol.

10. A process according to claim 7 wherein said extractant solvent is ethylene glycol.

11. A process according to claim 7 wherein said extractant solvent is propylene glycol.

12. A process according to claim 7 wherein said extractant solvent is glycerine.

13. A process according to claim 1 which is carried out in a continuous or semi continuous fashion.

* * * * *

UNITED STATES PATENT AND TRADEMARK OFFICE
CERTIFICATE OF CORRECTION

PATENT NO. : 4,153,516

DATED : May 8, 1979

INVENTOR(S) : Denvil E. Reed, et al

It is certified that error appears in the above–identified patent and that said Letters Patent are hereby corrected as shown below:

Columns 1 & 2 should be deleted to insert the attached Columns 1 thru 4 therefor.

THIS CERTIFICATE APPLYS TO THE GRANT, EXCLUSIVELY.

Signed and Sealed this

First Day of January 1980

[SEAL]

Attest:

SIDNEY A. DIAMOND

Attesting Officer

Commissioner of Patents and Trademarks

PROCESS FOR SEPARATING ALKOXYKETONE COMPOUNDS FROM THE CORRESPONDING 1-ALKOXY-2-ALKANOL COMPOUND

BACKGROUND OF THE INVENTION

This invention relates to a method recovering alkoxyketone compounds having a high degree of purity from a mixture of an alkoxyketone compound and the corresponding 1-alkoxy-2-alkanol compound.

The most common form of preparing alkoxyketone compounds is to catalytically dehydrogenate the corresponding 1-alkoxy-2-alkanol compound in the vapor phase. When such a preparative method is used, problems of separation arise. The difficulties surrounding the separation of an alkoxyketone compound from admixture with the corresponding 1-alkoxy-2-alkanol have been primarily due to the formation of a binary azeotrope composition.

This difficulty has been noted in the past and a variety of solutions have been proposed in an attempt to obtain alkoxyketone compounds of high purity. Heretofore, the separation has been effectuated either by chemical modification followed by distillation or by multistep azeotropic distillative methods. For example, U.S. Pat. No. 2,170,855 discloses a chemical modification method in which an organic acid or anhydride is added to a reaction mixture of an alkoxyacetone compound and the corresponding 1-alkoxy-2-propanol compound resulting in the formation of the high boiling ester derivative of the 1-alkoxy-2-propanol starting material. The resulting mixture is distilled and redistilled to recover the desired alkoxyacetone.

Alternatively, U.S. Pat. Nos. 2,795,873 and 3,525,735, respectively, discloses azeotropic distillation processes in which either an unsubstituted monohydric alcohol or water is added to the reaction mixture in order to break the minimum boiling point binary azeotrope. In these processes, a new lower boiling binary azeotrope is formed between the azeotropic solvents and the alkoxyacetone compound which may then be removed from the binary azeotropic mixture by distillation.

Although, they seem relatively simple and efficient, the prior art processes suffer from one or more inherent limitations and disadvantages. For example, it is generally recognized that both of the previously disclosed processes usually give rise to alkoxyketone compounds that are contaminated with unacceptable amounts of the corresponding 1-alkoxy-2-alkanol compound. In addition, the azeotropic distillation process requires large expenditures of energy due to the very high latent heat of the azeotropic solvents, as well as, time consuming and cumbersome purification procedures to remove the desired alkoxyketone compound from the azeotropic solvent. Consequently there exists a need for a fast and more efficient single step process for separating alkoxyketone compounds from the corresponding 1-alkoxy-2-alkanol compound with enhanced purity of the alkoxyketone compound coupled with low energy requirements.

SUMMARY OF THE INVENTION

According to the present invention there is provided a process for separating an alkoxyketone compound from a feed mixture of the alkoxyketone compound and the corresponding 1-alkoxy-2-alkanol compound which comprises:

A. introducing an extractant solvent selected from the group of aliphatic diol, triol and polyol compounds having from 2 to 6 carbon atoms and monohydric aliphatic alcohols having from 5 to 10 carbon atoms into an extractive distillation zone;

B. introducing the feed mixture into the extractive distillation zone at a point above the bottom thereof and below the extractant solvent point of entry;

C. subjecting the resulting mixture to extractive distillation in the extractive distillation zone; and D. recovering at the top of the extractive distillation zone a distillate fraction comprised of the alkoxyketone and the extractant solvent, substantially free of the corresponding 1-alkoxy-2-alkanol compound.

The process of this invention provides excellent separation under mild process conditions, using very little equipment and has the advantage of very short separation times and minimum energy expenditures.

BRIEF DESCRIPTION OF THE DRAWING

The FIGURE is a schematic flow diagram of an illustrative embodiment of the present invention.

DESCRIPTION OF THE PREFERRED EMBODIMENTS

The alkoxyketone compounds contemplated for use in the process of this invention are lower alkoxyketone compounds having from 4 to 10 carbon atoms. Illustrative of alkoxyketone compounds which can be separated from the corresponding 1-alkoxy-2-alkanol compound are methoxyacetone, ethoxyacetone, n-proproxyacetone, isopropoxyacetone, n-butoxyacetone, tert-butoxyacetone, methoxy-2-butanone, ethoxy-2-butanone and the like.

Compounds which are useful as extractant solvents in the conduct of the process of this invention are diol or triol or polyol compounds which contain from 2 to about 6 carbon atoms. Preferred extractant solvents are diol or triol compounds having from 2 to about 6 carbon atoms, with those diol compounds having 2 or 3 carbon atoms and glycerine being particularly preferred. Illustrative of useful extractant solvents are linear diol compounds such as ethylene glycol; 1,2-propylene glycol; 1,3-propylene glycol, 1,2-dihydroxypentane; 1,3-butanediol, 1,4-butanediol, 2,3-dihydroxypentane, 1,3-dihydroxypentane; 2,4-pentanediol, 1,5-pentanediol, 1,2-dihydroxy-3-methylpentane, 1,6-hexanediol, 1,2-hexanediol, 2,5-hexanediol and the like. Illustrative of useful cyclic diols are 1,2-cyclopentanediol; 1,2-dihydroxy-4-ethyl-5-propylcyclohexane and the like. Useful triol extractant solvents include glycerine, 2,4,6-trihydroxyhexane, 1,2,6-hexanetriol or the like.

Still other suitable extractant solvents are monohydric primary aliphatic alcohols having from 5 to about 8 carbon atoms; monohydric aliphatic secondary alcohols having from 5 to about 8 carbon atoms and alicyclic alcohols having 5 or 6 carbon atoms in the ring with a total of from 6 to about 8 carbon atoms. Illustrative of useful monhydric extractant solvents are pentanols, hexanols, heptanols, octanols, secondary pentanols, secondary hexanols, cyclopentanols and cyclohexanols.

The ratio of feed mixture to the extractant solvent which is employed to effectuate the desired separation is not narrowly critical. It will be appreciated that this ratio may vary depending upon the particular extractant solvent employed, the composition of the feed mix-